(12) United States Patent
Lee et al.

(10) Patent No.: US 9,546,124 B2
(45) Date of Patent: Jan. 17, 2017

(54) METHOD FOR PRODUCING ACRYLIC ACID FROM GLYCEROL

(71) Applicant: LG CHEM, LTD., Seoul (KR)

(72) Inventors: Won Jae Lee, Daejeon (KR); Yong-Jin Choe, Daejeon (KR); Hyun Nam, Daejeon (KR); Myungjin Kong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/892,849

(22) PCT Filed: Jun. 27, 2014

(86) PCT No.: PCT/KR2014/005757
§ 371 (c)(1),
(2) Date: Nov. 20, 2015

(87) PCT Pub. No.: WO2014/209065
PCT Pub. Date: Dec. 31, 2014

(65) Prior Publication Data
US 2016/0122272 A1    May 5, 2016

(30) Foreign Application Priority Data

Jun. 27, 2013  (KR) ................ 10-2013-0074507
Jul. 8, 2013   (KR) ................ 10-2013-0079794
Jun. 27, 2014  (KR) ................ 10-2014-0079749

(51) Int. Cl.
| | |
|---|---|
| *C07C 51/41* | (2006.01) |
| *B01J 23/66* | (2006.01) |
| *B01J 23/68* | (2006.01) |
| *C07C 29/60* | (2006.01) |
| *C07C 51/25* | (2006.01) |
| *C07C 51/377* | (2006.01) |
| *B01J 23/52* | (2006.01) |

(52) U.S. Cl.
CPC .............. *C07C 51/41* (2013.01); *B01J 23/66* (2013.01); *B01J 23/68* (2013.01); *C07C 29/60* (2013.01); *C07C 51/25* (2013.01); *C07C 51/377* (2013.01); *B01J 23/52* (2013.01)

(58) Field of Classification Search
CPC .................................................... C07C 51/41
USPC ....................................................... 562/599
See application file for complete search history.

(56) References Cited

U.S. PATENT DOCUMENTS

| | | | |
|---|---|---|---|
| 4,072,727 A | 2/1978 | Vanderspurt | |
| 5,892,066 A | 4/1999 | Grey | |
| 7,396,962 B1 | 7/2008 | Dubois et al. | |
| 7,655,818 B2 | 2/2010 | Dubois et al. | |
| 7,683,220 B2 | 3/2010 | Matsunami et al. | |
| 7,718,829 B2 | 5/2010 | Masaaki et al. | |
| 7,951,978 B2 | 5/2011 | Arita et al. | |
| 8,198,481 B2 * | 6/2012 | Kuppinger ............ C07C 51/377 |
| | | | 562/600 |
| 2009/0287004 A1 | 11/2009 | Bergman et al. | |

FOREIGN PATENT DOCUMENTS

| | | |
|---|---|---|
| EP | 2241549 A1 | 10/2010 |
| JP | 2010-501526 A | 1/2010 |
| KR | 10-2009-0057612 A | 6/2009 |
| WO | 2005/073160 A1 | 11/2005 |
| WO | 2008/092115 A1 | 7/2008 |
| WO | 2013/017942 A2 | 2/2013 |

OTHER PUBLICATIONS

"Rhenium-Catalyzed Transfer Hydrogenation and Deoxygenation of Biomass-Derived Polyols to Small and Useful Organics", Jing Yi, et al., ChemSusChem 2012, 5, 1401-1404.
"Deoxygenation of Biomass-Derived Feedstocks: Oxorhenium-Catalyzed Deoxydehydration of Sugars and Sugar Alcohols**", Mika Shiramizu, et al, Angew. Chem. Int. Ed. 2012, 51, 8082-8086.
"Enhanced performance of the catalytic conversion of allyl alcohol to 3-hydroxypropionic acid using bimetallic gold catalysts", Ermelinda Falletta, et al., The Royal Society of Chemistry 2011.
Pina, et al.: "Oxidation of Allyl Alcohol in the Presence of a Gold Catalyst: A Route to 3-Hydroxypropionic Acid", ChemSusChem, 2009, pp. 57-58.

* cited by examiner

*Primary Examiner* — Sikarl Witherspoon
(74) *Attorney, Agent, or Firm* — Dentons US LLP

(57) ABSTRACT

Disclosed is a method of preparing acrylic acid from glycerol, including: (a) preparing products including allyl alcohol from reactants including glycerol and carboxylic acid; (b) adding a heterogeneous catalyst and a basic solution to the product including allyl alcohol and then performing oxidation, thus preparing a mixture composed of 3-hydroxypropionic acid and acrylic acid; (c) dehydrating 3-hydroxypropionic acid of the mixture composed of 3-hydroxypropionic acid and acrylic acid, thus producing acrylic acid.

17 Claims, No Drawings

METHOD FOR PRODUCING ACRYLIC ACID FROM GLYCEROL

This application is a National Stage Entry of International Application No. PCT/KR2014/005757, filed Jun. 27, 2014, and claims the benefit of Korean Application No. 10-2013-0074507, filed on Jun. 27, 2013, Korean Application No. 10-2013-0079794, filed Jul. 8, 2013, and Korean Application No. 10-2014-0079749, filed Jun. 27, 2014, all of which are hereby incorporated by reference in their entirety for all purposes as if fully set forth herein.

TECHNICAL FIELD

The present invention relates to a method of preparing acrylic acid from glycerol and, more particularly, to a method of preparing acrylic acid through 3-hydroxypropionic acid from glycerol.

BACKGROUND ART

Currently industrially useful as preparation of acrylic acid is a preparation method including bringing propylene produced by a petrochemical process into contact with a molecular oxygen-containing gas so as to oxidize it. Specifically, acrylic acid is prepared via a two-step reaction mechanism including a first step for gas oxidation of propylene into acrolein by a molecular oxygen-containing gas and a second step for additional oxidation of a reactive gas containing the acrolein into acrylic acid.

Meanwhile, methods of preparing acrylic acid from a biomass-derived material due to fossil fuel exhaustion are receiving great attention. Among biomass-derived materials, glycerol is obtained as a byproduct in the course of producing biodiesel from vegetable or animal oil. Biodiesel synthesis techniques have been already commercialized, and the demand thereof is increasing every year. Glycerol may be used in a large amount, and is renewable and eco-friendly because it may be safely stored and transported without the risk of explosion and toxicity. Hence, glycerol is considered to be a promising material for preparing acrylic acid.

Thus, there is an urgent need for a novel method of preparing acrylic acid from glycerol that is a byproduct of a biodiesel synthesis process.

DISCLOSURE

Technical Problem

The present invention has been made keeping in mind the above problems encountered in the related art, and an object of the present invention is to provide a novel method of preparing acrylic acid from glycerol that is a byproduct of a biodiesel synthesis process.

Technical Solution

In order to accomplish the above object, the present invention provides a novel method of preparing acrylic acid from glycerol, comprising: preparing products including allyl alcohol from reactants including glycerol and carboxylic acid; adding a heterogeneous catalyst and a basic solution to the product including allyl alcohol and then performing oxidation to give a mixture comprising 3-hydroxypropionic acid and acrylic acid; and dehydrating 3-hydroxypropionic acid of the mixture comprising 3-hydroxypropionic acid and acrylic acid to give acrylic acid.

Advantageous Effects

According to the present invention, a novel method of preparing acrylic acid from glycerol is eco-friendly because of the use of glycerol, which is a byproduct of a biodiesel synthesis process, along with safe storage or transport thereof.

BEST MODE

Hereinafter, a detailed description will be given of a method of preparing acrylic acid from glycerol according to the present invention.

According to the present invention, the method of preparing acrylic acid from glycerol comprises: (a) preparing products including allyl alcohol from reactants including glycerol and carboxylic acid; (b) adding a heterogeneous catalyst and a basic solution to the product including allyl alcohol and then performing oxidation to give a mixture comprising 3-hydroxypropionic acid and acrylic acid; and (c) dehydrating 3-hydroxypropionic acid of the mixture comprising 3-hydroxypropionic acid and acrylic acid to give acrylic acid.

Glycerol is a compound represented by $HOCH_2(CHOH)CH_2OH$, and is also referred to as trihydroxypropane or glycerin. The purity of glycerol does not limit the scope of the present invention, but is set to 80 wt % or more, preferably 90 wt % or more, and more preferably 95 wt % or more, in order to reduce the production of reaction byproducts.

In the present invention, the inventors utilized the glycerol which can be obtained as a byproduct from a biodiesel synthesis process via transesterification of vegetable oil and alcohol.

In the present invention, (a) preparing products including allyl alcohol from reactants including glycerol and carboxylic acid is carried out as shown in Scheme 1 below.

[Scheme 1]

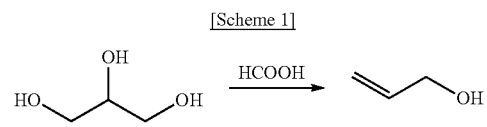

As shown in Scheme 1, since glycerol and formic acid react at 1:1, the equivalent amount herein refers to a molar amount.

Although carboxylic acid is exemplified by formic acid in Scheme 1, it is not necessarily limited to formic acid. However, formic acid is desirable in terms of easy removal of carbon dioxide, which is generated as a byproduct of a reaction for producing allyl alcohol.

Formic acid may be prepared from a formic acid salt. The formic acid salt may be sodium formate or calcium formate. Particularly useful is sodium formate or calcium formate, which is obtained as a byproduct during production of polyhydric alcohol. The polyhydric alcohol includes, but is not limited to, pentaerythritol, trimethylolethane, trimethylolpropane, or neopentyl glycol.

Formic acid may be prepared from formic acid ester. The formic acid ester includes, but is not limited to, methyl formate or ethyl formate.

In the step (a) oxidative decomposition of glycerol or carbonization may occur in an oxygen-containing gas atmosphere, which may result in lowering the product yield. Therefore, the step (a) is performed in an inert gas atmosphere, for example, in a helium, nitrogen or argon atmosphere.

Also, the step (a) is conducted at a reaction temperature of 220~260° C., preferably 220~250° C., and more preferably 230~250° C., thereby producing allyl alcohol at high yield from glycerol.

In the step (a), formic acid is added in an amount of 0.5~3 equivalents relative to 1 equivalent of glycerol. To increase the yield of allyl alcohol, formic acid is preferably added in an amount of 0.8~2 equivalents, and more preferably 1.2~1.7 equivalents.

In the present invention, the step (a) is performed without using a catalyst disclosed in ChemSusChem 2012, Vol 5, pp 1401-1404 and thus does not generate byproducts such as propionaldehyde or 1,3-dihydroxyacetone, and is a non-catalytic reaction without the use of an expensive rhenium catalyst disclosed in Angew. Chem. Int. Ed. 2012, Vol 51, pp 8082-8086, and is thus appropriate for industrial mass production.

The amount of allyl alcohol produced in the step (a) is preferably 30 wt % or more based on the total weight of the product including allyl alcohol.

In the present invention, the step (b) adding a heterogeneous catalyst and a basic solution to the product including allyl alcohol and then performing oxidation to give a mixture comprising 3-hydroxypropionic acid and acrylic acid is performed as shown in Scheme 2 below.

[Scheme 2]

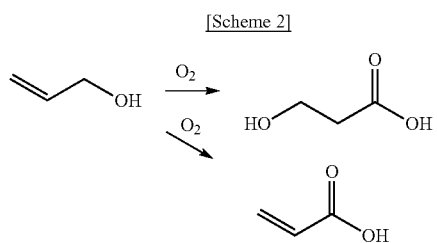

In the step (b), allyl alcohol may be used as a reactant in concentrated form, or a solution including water, a base, etc. or a solution including the reaction byproducts obtained in the step (a) may be used. As such, allyl alcohol has a concentration of 0.1~90 mol %.

In the step (b), oxygen or an oxygen-containing gas may be fed to the reactor, thereby increasing oxidation reactivity and obtaining 3-hydroxypropionic acid and acrylic acid at high yield. The partial oxygen pressure of oxygen or an oxygen-containing gas may be set out of the combustion range and the explosion range, taking into account the reactant concentration and the reaction temperature. The partial oxygen pressure is 1~50 atm, preferably 1~30 atm, and more preferably 1~20 atm, based on an absolute pressure. The reaction temperature is not particularly limited so long as the reaction is carried out in a liquid phase, but is set to 10~120° C., preferably 20~100° C., and more preferably 30~90° C.

In the step (b), the catalyst is a heterogeneous catalyst comprising gold having a size of 5 nm or less loaded on a carrier. As used herein, the heterogeneous catalyst refers to a catalyst that is in a different phase from the reactants, and is favorable because the catalyst may be easily separated from the product after reaction.

Thus, the catalyst according to the present invention is configured such that gold having a size of 5 nm or less and preferably 1 nm or less is loaded on a carrier. When the particle size of gold falls in the above range, superior reactivity and selectivity may be obtained. As the particle size of gold decreases, the yield of acrylic acid and 3-hydroxypropionic acid products may increase. Particularly when the particle size of gold is 1 nm or less, the yield of acrylic acid as a main product may reach 50%.

Also, gold is used in an amount of 5 wt % or less, and preferably 0.0001~5 wt %, based on the total dry weight of the carrier. Given the above range, reactivity may be maximized while minimizing the use of precious metal gold.

The carrier may include at least one selected from the group consisting of activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), tungsten oxide ($WO_3$), and cerium oxide ($CeO_2$). The carrier preferably includes, but is not limited to, cerium oxide ($CeO_2$) or a composite oxide containing cerium oxide.

According to the present invention, when the catalyst is subjected to special pretreatment, the durability of the catalyst is improved and thus it may be reused several times. The pretreatment temperature is 50~500° C., and preferably 70~400° C. The pretreatment time is 10 min~24 hr, and preferably 20 min~20 hr. The gas used for pretreatment may include oxygen, nitrogen, helium and argon, which may be used alone or in combination.

In the step (b), the basic solution is used. The basic solution activates the oxidation reaction of allyl alcohol. The basic solution may be prepared by mixing a basic compound containing an alkali metal or alkaline earth metal with water. Specifically, the basic compound may include at least one selected from the group consisting of sodium hydroxide, lithium hydroxide, potassium hydroxide, and calcium hydroxide.

The basic compound of the basic solution is added at a molar ratio of 0.01~10 and preferably 2~8 relative to 1 mol of allyl alcohol. The amount of added basic compound may affect the conversion of allyl alcohol, and the yield and selectivity of acrylic acid, 3-hydroxypropionic acid, and a byproduct of glyceric acid.

In the present invention, the step (c) dehydrating 3-hydroxypropionic acid of the mixture comprising 3-hydroxypropionic acid and acrylic acid to give acrylic acid is performed as shown in Scheme 3 below.

[Scheme 3]

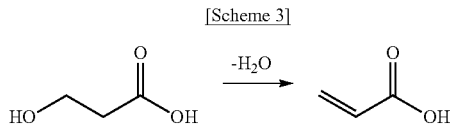

In the step (c), 3-hydroxypropionic acid may be used as the reactant. It may be obtained by separating the mixture comprising 3-hydroxypropionic acid and acrylic acid obtained in the step (b) or by concentrating 3-hydroxypropionic acid. Alternatively, the mixture comprising 3-hydroxypropionic acid and acrylic acid may be used as it is.

The method of the present invention may further comprise the process of separating the mixture comprising 3-hydroxypropionic acid and acrylic acid, before the step (c). Separating the mixture comprising 3-hydroxypropionic acid and acrylic acid is carried out as follows.

Separating the mixture comprising 3-hydroxypropionic acid and acrylic acid may be conducted using at least one selected among extraction, crystallization, and distillation.

Separating 3-hydroxypropionic acid from the mixture comprising 3-hydroxypropionic acid and acrylic acid may be performed using extraction.

A solvent used for extraction may include, but is not limited to, at least one selected from among alcohol, aldehyde, ketone, ether, ester, an aromatic compound, and other organic solvents.

Separating 3-hydroxypropionic acid from the mixture comprising 3-hydroxypropionic acid and acrylic acid may be conducted using crystallization.

Crystallization is a separation process using solubility difference of the mixture, and may be performed using suspension crystallization or layer crystallization.

Separating 3-hydroxypropionic acid from the mixture comprising 3-hydroxypropionic acid and acrylic acid may be conducted using distillation.

Distillation is a separation process using boiling point difference of the mixture and may be carried out at below the atmospheric pressure or atmospheric pressure or above the atmospheric pressure. To increase separation efficiency, a solvent may be added. In order to simultaneously implement reaction and separation, reactive distillation may be applied.

As such, a dehydration catalyst is provided in the distillation tower, thus separating the mixture while converting 3-hydroxypropionic acid into acrylic acid.

The purity of 3-hydroxypropionic acid separated from the mixture comprising 3-hydroxypropionic acid and acrylic acid may be 70% or more.

The step (c) may be performed via dehydration using a catalyst, and the catalyst may be an acidic catalyst or a basic catalyst. The acidic catalyst may be exemplified by a catalyst including a natural or synthetic silica material, acidic zeolite, heteropolyacid, and an acidic ion exchange resin; a metal phosphate catalyst including at least one selected from the group consisting of chromium, manganese, iron, cobalt, nickel, boron, lanthanum, calcium, strontium, barium, molybdenum, and ruthenium metals, and a metal phosphate catalyst loaded on a carrier comprising $TiO_2$, $Al_2O_3$, $SiO_2$, or $SiO_2$—$Al_2O_3$; at least one metal oxide selected from the group consisting of $TiO_2$, $Al_2O_3$, $SiO_2$, $ZrO_2$, $SnO_2$, $Ta_2O_3$, $Nb_2O_5$, and $SiO_2$—$Al_2O_3$; any one composite oxide selected from the group consisting of $ZrO_2$—$SO_4$, $ZrO_2$—$PO_4$, $ZrO_2$—$WO_3$, $ZrO_2$—$SiO_2$, $TiO_2$—$SO_4$, $TnO_2$—$SO_4$, $H_3PO_4$—$Al_2O_3$, $H_3PO_4$—$SiO_2$, and $H_3PO_4$—$ZrO_2$; or a catalyst including at least one selected from the group consisting of inorganic acids, including hydrochloric acid, sulfuric acid, nitric acid, and phosphoric acid.

The basic catalyst may be a catalyst including at least one selected from the group consisting of alkali metal or alkaline earth metal oxides and hydroxides; amines such as trimethylamine, triethylamine and tridodecyl amine; and basic ion exchange resins.

In the step (c), the reaction temperature is 70~300° C., and preferably 100~280° C. The reaction pressure may be below the atmospheric pressure or atmospheric pressure or above the atmospheric pressure. Also, the yield of acrylic acid from 3-hydroxypropionic acid is 90% or more, preferably 92% or more, and more preferably 95% or more.

In the present invention, three reaction steps as shown in Scheme 1, Scheme 2, and Scheme 3 may be carried out using any one reactor or a reactor combination of two or more selected from the group consisting of a batch reactor, a semi-batch reactor, a continuous stirred tank reactor, a plug flow reactor, a fixed-bed reactor, and a fluidized-bed reactor.

MODE FOR INVENTION

The following examples of the present invention are disclosed for illustrative purposes, but those skilled in the art will appreciate that various modifications, additions and substitutions are possible, without departing from the scope and spirit of the invention as disclosed in the accompanying claims.

EXAMPLE

Preparation of Oxidation Catalyst

Synthesis Example 12 mg of $HAuCl_4 \cdot 3H_2O$ was dissolved in 100 mL of distilled water, and pH of the solution was adjusted to 10 using a 0.2 M sodium hydroxide aqueous solution. Subsequently, 190 mg of cerium oxide was dispersed in the solution, and the resulting solution was maintained at 70° C. for 1, 3, 6, and 12 hr with stirring. The solution was filtered, washed and dried to obtain the catalyst.

Preparation of Allyl Alcohol from Glycerol Step (a)

Example 1

In a flask reactor (F1) in a helium atmosphere, 27.6 g (300 mmol) of glycerol and 20.71 g (450 mmol) of formic acid were placed, and heated to 230° C. at a rate of 230° C./hr with slow stirring, yielding allyl alcohol.

Example 2

Allyl alcohol was prepared in the same manner as in Example 1, with the exception that 11.04 g (240 mmol) of formic acid was added.

Preparation of 3-Hydroxypropionic Acid and Acrylic Acid from Allyl Alcohol Step (b)

Example 3

1.17 mL of allyl alcohol was mixed with 2.07 g of sodium hydroxide and 17.24 mL of distilled water. As such, sodium hydroxide was used in an amount of 3 mol relative to 1 mol of allyl alcohol. While the mixed solution was slowly stirred, 30 mg of the oxidation catalyst prepared maintaining the solution for 1 hr in Synthesis Example was added.

While oxygen, of which partial pressure was 3 atm was injected into the reactor, the temperature of the reactor was elevated to 50° C. and then the reaction was carried out for 24 hr, yielding 3-hydroxypropionic acid and acrylic acid.

Example 4

3-hydroxypropionic acid and acrylic acid were prepared in the same manner as in Example 3, with the exception that the oxidation catalyst prepared by maintaining the synthesis time for 3 hr in Synthesis Example was used.

Comparative Example 1

The reaction was carried out in the same manner as in Example 3, with the exception that the catalyst prepared using only gold particles without a carrier was added to the mixed solution.

Comparative Example 2

The reaction was carried out in the same manner as in Example 3, with the exception that the catalyst prepared using an activated carbon carrier was added to the mixed solution.

Preparation of Acrylic Acid from 3-Hydroxypropionic Acid Step (c)

Example 5

3-hydroxypropionic acid was added with 100 g of phosphoric acid, and then heated to 180° C. While bubbling nitrogen via a gas distributor placed at the bottom of the reactor, a 50 wt % of 3-hydroxypropionic acid aqueous solution was added slowly at a rate of 0.5 g/min into the reactor. The vaporized product was passed through a condenser connected to the reactor, and then the condensate was collected in a flask placed at the end of the condenser.

Example 6

8 g of a $TiO_2$ catalyst was loaded in a fixed-bed reactor, the temperature of the reactor was elevated to 180° C., and then a 10 wt % of 3-hydroxypropionic acid aqueous solution was fed from the top of the reactor at a rate of 3.0 g/hr. The product was passed through a condenser placed at the end of the reactor and then collected in a flask.

Test Example

The reaction products obtained in the above examples and comparative examples were analyzed for calculation of conversion and selectivity as follows.

The concentration of allyl alcohol prepared in the step (a) and unreacted glycerol was analyzed using gas chromatography (GC 6890N, Agilent).

Based on such measurement results, glycerol conversion, allyl alcohol selectivity, and allyl alcohol yield were calculated using Equations 1 to 3 below. The results are shown in Table 2 below.

Glycerol conversion (%)=100×(mol of glycerol before reaction−mol of glycerol after reaction)/(mol of glycerol before reaction)   [Equation 1]

Allyl alcohol selectivity (%)=100×(mol of produced allyl alcohol)/(mol of reacted glycerol)   [Equation 2]

Allyl alcohol yield (%)=(glycerol conversion×allyl alcohol selectivity)/100   [Equation 3]

For the liquid reaction product obtained in the step (b), HPLC area % of allyl alcohol, acrylic acid and 3-hydroxypropionic acid was analyzed using liquid chromatography (YL9100 HPLC, Young Lin Instrument Co.). Allyl alcohol conversion, 3-hydroxypropionic acid yield, and acrylic acid yield were calculated using Equations 4 to 6 below.

Allyl alcohol conversion (%)=100×(mol of allyl alcohol before reaction−mol of allyl alcohol after reaction)/(mol of allyl alcohol before reaction)   [Equation 4]

3-Hydroxypropionic acid yield (%)=100×(mol of 3-hydroxypropionic acid produced)/(mol of allyl alcohol before reaction)   [Equation 5]

Acrylic acid yield (%)=100×(mol of acrylic acid produced)/(mol of allyl alcohol before reaction)   [Equation 6]

For the liquid reaction product obtained in the step (c), HPLC area % of acrylic acid and 3-hydroxypropionic acid was analyzed using liquid chromatography (YL9100 HPLC, Young Lin Instrument Co.). Acrylic acid conversion, 3-hydroxypropionic acid selectivity, and 3-hydroxypropionic acid yield were calculated using Equations 7 to 9 below.

3-Hydroxypropionic acid conversion (%)=100×(mol of 3-hydroxypropionic acid before reaction−mol of 3-hydroxypropionic acid after reaction)/(mol of 3-hydroxypropionic acid before reaction)   [Equation 7]

Acrylic acid selectivity (%)=100×(mol of produced acrylic acid)/(mol of reacted 3-hydroxypropionic acid)   [Equation 8]

Acrylic acid yield (%)=(3-hydroxypropionic acid conversion×acrylic acid selectivity)/100   [Equation 9]

The gold particle size of the oxidation catalyst obtained in Synthesis Example was measured using a transmission electron microscope (JEM-2100, JEOL). When the synthesis time was 1, 3, 6, and 12 hr, the average particle size of gold was 5 nm or less. Also, the amount of gold of the oxidation catalyst was 5 wt % or less based on the total dry weight of the carrier.

Test Example 1

Test Results in the Step (a)

The glycerol conversion, allyl alcohol selectivity and allyl alcohol yield in the step (a) for preparing allyl alcohol from glycerol are shown in Table 1 below. As the mol of formic acid was higher, the glycerol conversion was increased. On the other hand, as the mol of formic acid was lower, the glycerol conversion was decreased but the allyl alcohol selectivity was increased.

TABLE 1

|  | Glycerol Conversion, % | Allyl alcohol Selectivity, % | Allyl alcohol Yield, % |
|---|---|---|---|
| Ex. 1 | 95 | 85 | 80.7 |
| Ex. 2 | 72 | 89 | 64.1 |

Test Example 2

Test Results in the Step (b)

The allyl alcohol conversion, 3-hydroxypropionic acid yield and acrylic acid yield in the step (b) for preparing 3-hydroxypropionic acid and acrylic acid from allyl alcohol are shown in Table 2 below. As the synthesis time was longer, the 3-hydroxypropionic acid yield and the acrylic acid yield were increased. In Comparative Examples 1 and 2 without the use of a carrier or with the use of an activated carbon carrier, the 3-hydroxypropionic acid yield and the acrylic acid yield were remarkably decreased.

TABLE 2

| | Allyl alcohol Conversion, % | 3-Hydroxypropionic acid Yield, % | Acrylic acid Yield, % |
|---|---|---|---|
| Ex. 3 | 100 | 28.4 | 51.1 |
| Ex. 4 | 100 | 24.1 | 43.1 |
| C. Ex. 1 | 49.6 | 4.2 | 0.0 |
| C. Ex. 2 | 100 | 18.5 | 0.8 |

Test Example 3

Test Results in the Step (c)

The 3-hydroxypropionic acid conversion, acrylic acid selectivity and acrylic acid yield in the step (c) for preparing acrylic acid from 3-hydroxypropionic acid are shown in Table 3 below. In Examples 5 and 6 using the acidic catalyst, the acrylic acid yield was 90% or more.

TABLE 3

| | 3-Hydroxypropionic acid Conversion, % | Acrylic acid Selectivity, % | Acrylic acid Yield, % |
|---|---|---|---|
| Ex. 5 | 97 | 94 | 91.1 |
| Ex. 6 | 95 | 96 | 91.2 |

The invention claimed is:

1. A method of comprising acrylic acid from glycerol, comprising:
   (a) preparing products including allyl alcohol from reactants comprising glycerol and carboxylic acid;
   (b) adding a heterogeneous catalyst and a basic solution to the product comprising allyl alcohol and then performing oxidation, thus preparing a mixture comprising 3-hydroxypropionic acid and acrylic acid;
   (c) dehydrating 3-hydroxypropionic acid of the mixture comprising 3-hydroxypropionic acid and acrylic acid, thus producing acrylic acid,
   wherein the heterogeneous catalyst of (b) is configured such that gold having a size of 5 nm or less is loaded on a carrier, and
   wherein the carrier is cerium oxide ($CeO_2$).

2. The method of claim 1, further comprising separating the mixture comprising 3-hydroxypropionic acid and acrylic acid, before (c).

3. The method of claim 1, wherein (a) is performed at 220~260° C. using glycerol and carboxylic acid in an amount of 0.5~2 equivalents relative to 1 equivalent of glycerol.

4. The method of claim 1, wherein the oxidation in (b) is performed at 10~120° C. under a partial oxygen pressure of 0.01~50 atm based on an absolute pressure by feeding oxygen or an oxygen-containing gas.

5. The method of claim 1, wherein the gold of the heterogeneous catalyst is used in an amount of 5 wt % or less based on a total dry weight of the carrier.

6. The method of claim 1, wherein in (b), the basic solution is prepared by mixing a basic compound containing an alkali metal or alkaline earth metal with water.

7. The method of claim 6, wherein the basic compound comprises at least one selected from the group consisting of sodium hydroxide, lithium hydroxide, potassium hydroxide, and calcium hydroxide.

8. The method of claim 1, wherein in (a), the carboxylic acid is formic acid.

9. The method of claim 1, wherein an amount of allyl alcohol produced in (a) is 30 wt % or more based on a total weight of the product including allyl alcohol.

10. The method of claim 2, wherein separating the mixture comprising 3-hydroxypropionic acid and acrylic acid is performed using at least one process selected from the group consisting of extraction, crystallization, and distillation.

11. The method of claim 10, wherein the separated 3-hydroxypropionic acid or acrylic acid has a purity of 70% or more.

12. The method of claim 1, wherein (c) is performed at 70~300° C.

13. The method of claim 1, wherein (c) is performed using an acidic catalyst or a basic catalyst.

14. The method of claim 13, wherein the acidic catalyst is a catalyst comprising a natural or synthetic silica material, acidic zeolite, heteropolyacid, and an acidic ion exchange resin; a metal phosphate catalyst comprising at least one selected from the group consisting of chromium, manganese, iron, cobalt, nickel, boron, lanthanum, calcium, strontium, barium, molybdenum, and ruthenium metals, and a metal phosphate catalyst loaded on a carrier comprising $TiO_2$, $Al_2O_3$, $SiO_2$, or $SiO_2$—$Al_2O_3$; at least one metal oxide selected from the group consisting of $TiO_2$, $Al_2O_3$, $SiO_2$, $ZrO_2$, $SnO_2$, $Ta_2O_3$, $Nb_2O_5$, and $SiO_2$—$Al_2O_3$; any one composite oxide selected from the group consisting of $ZrO_2$—$SO_4$, $ZrO_2$—$PO_4$, $ZrO_2$—$WO_3$, $ZrO_2$—$SiO_2$, $TiO_2$—$SO_4$, $TnO_2$—$SO_4$, $H_3PO_4$—$Al_2O_3$, $H_3PO_4$—$SiO_2$, and $H_3PO_4$—$ZrO_2$; or a catalyst comprising at least one selected from the group consisting of inorganic acids, comprising hydrochloric acid, sulfuric acid, nitric acid, and phosphoric acid.

15. The method of claim 13, wherein the basic catalyst is a catalyst comprising at least one selected from the group consisting of alkali metal or alkaline earth metal oxides and hydroxides; amines comprising trimethylamine, triethylamine and tridodecyl amine; and basic ion exchange resins.

16. The method of claim 13, wherein (c) is performed using any one reactor or a reactor combination of two or more selected from the group consisting of a batch reactor, a semi-batch reactor, a continuous stirred tank reactor, a plug flow reactor, a fixed-bed reactor, and a fluidized-bed reactor.

17. The method of claim 1, wherein in (c), acrylic acid is produced at a yield of 80% or more from 3-hydroxypropionic acid.

* * * * *